United States Patent
Liu

(10) Patent No.: US 9,113,659 B2
(45) Date of Patent: Aug. 25, 2015

(54) ELECTRONIC CIGARETTE AND ITS NOZZLE

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD., SHENZHEN BRANCH, Shenzhen, Guangdong Province (CN)

(*) Notice: Subject to any disclaimer, the term of this patent is extended or adjusted under 35 U.S.C. 154(b) by 74 days.

(21) Appl. No.: 13/879,385

(22) PCT Filed: Dec. 27, 2012

(86) PCT No.: PCT/CN2012/087720
§ 371 (c)(1),
(2) Date: Apr. 12, 2013

(87) PCT Pub. No.: WO2014/101059
PCT Pub. Date: Jul. 3, 2014

(65) Prior Publication Data
US 2014/0318558 A1 Oct. 30, 2014

(51) Int. Cl.
*A24F 47/00* (2006.01)
*A61M 15/06* (2006.01)

(52) U.S. Cl.
CPC ............. *A24F 47/008* (2013.01); *A24F 47/002* (2013.01); *A61M 15/06* (2013.01)

(58) Field of Classification Search
CPC ....... A24F 47/002; A24F 7/008; A61M 15/06
USPC ............................. 131/273, 329; 128/202.21
See application file for complete search history.

(56) References Cited

U.S. PATENT DOCUMENTS

| | | | | |
|---|---|---|---|---|
| 3,822,068 | A * | 7/1974 | Litherland | 277/529 |
| 2013/0213419 | A1 * | 8/2013 | Tucker et al. | 131/328 |
| 2013/0263869 | A1 * | 10/2013 | Zhu | 131/329 |
| 2014/0020696 | A1 * | 1/2014 | Liu | 131/329 |
| 2014/0076310 | A1 * | 3/2014 | Newton | 128/202.21 |
| 2014/0299139 | A1 * | 10/2014 | Liu | 131/329 |

* cited by examiner

*Primary Examiner* — Anthony Calandra
(74) *Attorney, Agent, or Firm* — Cheng-Ju Chiang

(57) ABSTRACT

The present invention provides an electronic cigarette and its nozzle, the electronic cigarette nozzle comprises an atomizer, a nozzle cover configured at an end of the atomizer, and further comprises a hermetic ring hermetically configured between the atomizer and the nozzle cover, the hermetic ring defines an concave chamber oriented to the atomizer, a thickness of the top wall of the concave chamber is gradually increased from a circumference to a center so that an upper surface of the top wall is a bevel, and plural through holes are circumferentially defined in the top wall. In the present invention, the hermetic ring, the concave chamber oriented to the atomizer, the top wall with a beveled upper surface and the plural through holes circumferentially defined in the bottom wall are adopted, and these technical means can eliminate the smoke oil residue, and improve user's taste experience.

12 Claims, 3 Drawing Sheets

ELECTRONIC CIGARETTE AND ITS NOZZLE

CROSS REFERENCE TO RELATED APPLICATIONS

The present application is a 35 U.S.C. §371 National Phase conversion of International (PCT) Patent Application No. PCT/CN2012/087720, filed on Dec. 27, 2012, the disclosure of which is incorporated by reference herein. The PCT International Patent Application was filed in Chinese.

TECHNICAL FIELD

This invention relates to a kind of electronic simulation cigarettes, and particularly to an electronic cigarette and its nozzle.

DESCRIPTION OF BACKGROUND

Electronic cigarettes are a kind of simulation cigarettes, which utilize the heating wire to heat up and atomize the flavor material to generate smog for user's inhalation.

Current electronic cigarettes have the following shortcomings: smoke oil is heated up in the atomizer to be vapor, and the vapor is cooled when it passes through the airflow passage within the nozzle which is relatively lower in temperature, and is partially liquefied into smoke oil and remains in the airflow passage, more and more smoke oil residue is gathered in the airflow passage, and even the users can inhale the smoke oil, this seriously affects the taste experience for users.

SUMMARY

A technical problem would be resolved in the present invention is: to provide an electronic cigarette nozzle, without residual smoke oil and having improved taste experience for users.

A further technical problem would be resolved in the present invention is: to provide an electronic cigarette, without residual smoke oil and having improved taste experience for users.

To resolve the above problems, the present invention provides the following technical solutions: an electronic cigarette nozzle, comprises an atomizer, and a nozzle cover configured at an end of the atomizer, characterized in that, the electronic cigarette nozzle further comprises a hermetic ring hermetically configured between the atomizer and the nozzle cover, the hermetic ring defines an concave chamber oriented to the atomizer, a thickness of the top wall of the concave chamber is gradually increased from a circumference to a center so that an upper surface of the top wall is a bevel, and plural through holes are circumferentially defined in the top wall.

Furthermore, the hermetic ring defines a circumferential slot oriented to the nozzle cover and coaxial with the concave chamber, for accommodating a side wall of the nozzle cover.

Furthermore, the slot is circumferentially configured with stripes on an outer surface of its side wall, to interferentially and hermetically engage with the atomizer.

Furthermore, the concave chamber on a lower surface of its top wall is configured with plural ribs having a pre-determined height and alternately arranged with the through holes, and the ribs have a pre-determined radial length.

Furthermore, the atomizer comprises a hollow tubular-shaped atomizing sleeve, an oil-storage cotton which is coaxially fixed within the atomizing sleeve and hollow tubular-shaped, a protection tube affixed to an inner wall of the oil-storage cotton, an atomizing unit configured within the protection tube and an atomizing seat hermetically fixed to an end of a tube constituted by the oil-storage cotton and the protection tube and remote from the nozzle cover.

Furthermore, the protection tube comprises a heat-resistant layer affixed onto the inner wall of the oil-storage cotton and coaxial with the oil-storage cotton, a first fiberglass tube coaxially configured at an inner side of the heat-resistant layer, and a second fiberglass tube affixed to an outer wall of the first fiberglass tube and an inner wall of the heat-resistant layer and located at an end facing to the nozzle cover, the first fiberglass tube has its one end inserted into the concave chamber of the hermetic ring, and the second fiberglass tube has its one end to abut against the atomizing unit.

Furthermore, the nozzle cover defines a suction hole, and the suction hole, a space defined by the nozzle cover and the top wall of the hermetical ring, the through holes of the hermetical ring, a space defined by adjacent ribs and having a pre-determined height, and the protection tube orderly constitute a smog passage.

Furthermore, the atomizing unit comprises an oil guiding member having its opposite ends to pass through the protection tube and abut against the oil-storage cotton, and a heating wire wound around the oil guiding member.

Furthermore, the atomizer is configured with a first connector at its end remote from the nozzle cover for mating with a power rod of the electronic cigarette, the first connector comprises a first connecting seat serving as a first electrode, a first pole coaxially configured within the first connecting seat and serving as a second electrode, and a first insulating sleeve configured between the first connecting seat and the first pole to insulate them.

Furthermore, lead wires connected with opposite ends of the heating wire pass through the first fiberglass tube, the atomizing seat and are respectively electrically connected with the first connecting seat and the first pole.

On the other hand, to resolve the above problems, the present invention further provides the following technical solutions: an electronic cigarette, the electronic cigarette comprises an electronic cigarette nozzle as above-described, and a power rod connected with the electronic cigarette nozzle.

Furthermore, the power rod is configured with a battery therein, and the power rod is further configured with a second connector at its end to mate with the electronic cigarette nozzle.

Furthermore, the second connector comprises a second connecting seat serving as a first electrode, a second pole coaxially configured within the first connecting seat and serving as a second electrode, a second insulating sleeve configured between the second connecting seat and the second pole to insulate them.

The beneficial effect of the present invention is that: the hermetic ring is hermetically configured between the atomizing sleeve of the atomizer and the nozzle cover, the hermetic ring is configured with a concave chamber oriented to the atomizer, the thickness of the top wall of the concave chamber is gradually increased from a circumference to a center so that an upper surface of the top wall is a bevel, and plural through holes are circumferentially defined in the top wall, these technical means can eliminate the smoke oil residue, and improve user's taste experience.

DETAILED DESCRIPTION OF THE EMBODIMENTS

It should be noted that, the embodiments and the characteristics in the embodiments can be mutually combined in case of no confliction. The embodiments of the present invention are further described in detail as follows in conjunction with the accompanying drawings.

Figure 1:
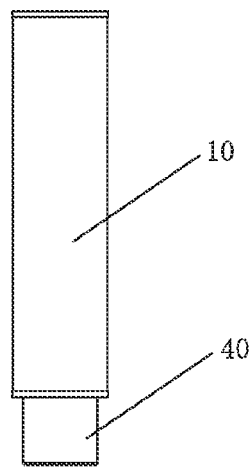
FIG. 1 is a front view of an electronic cigarette nozzle in accordance with an embodiment of the present invention.
Figure 2:
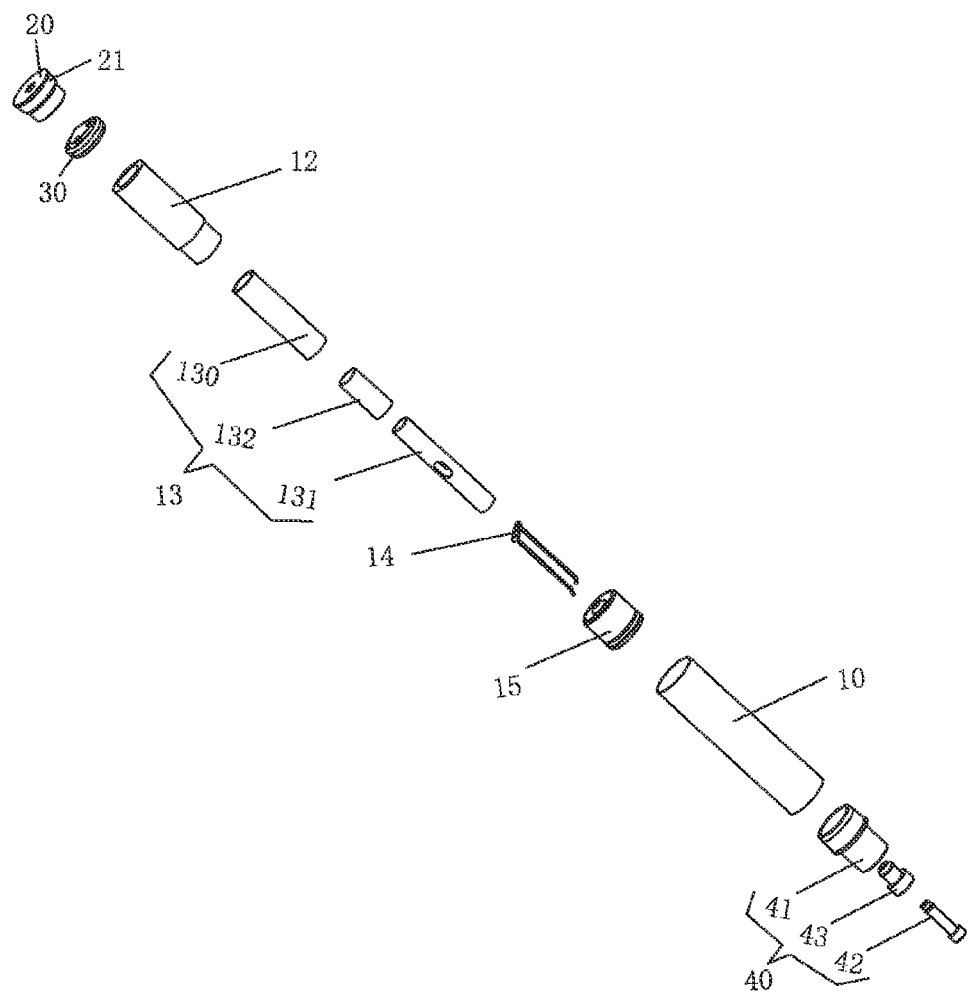
FIG. 2 is an exploded view of the electronic cigarette nozzle as shown in FIG. 1.
Figure 3:
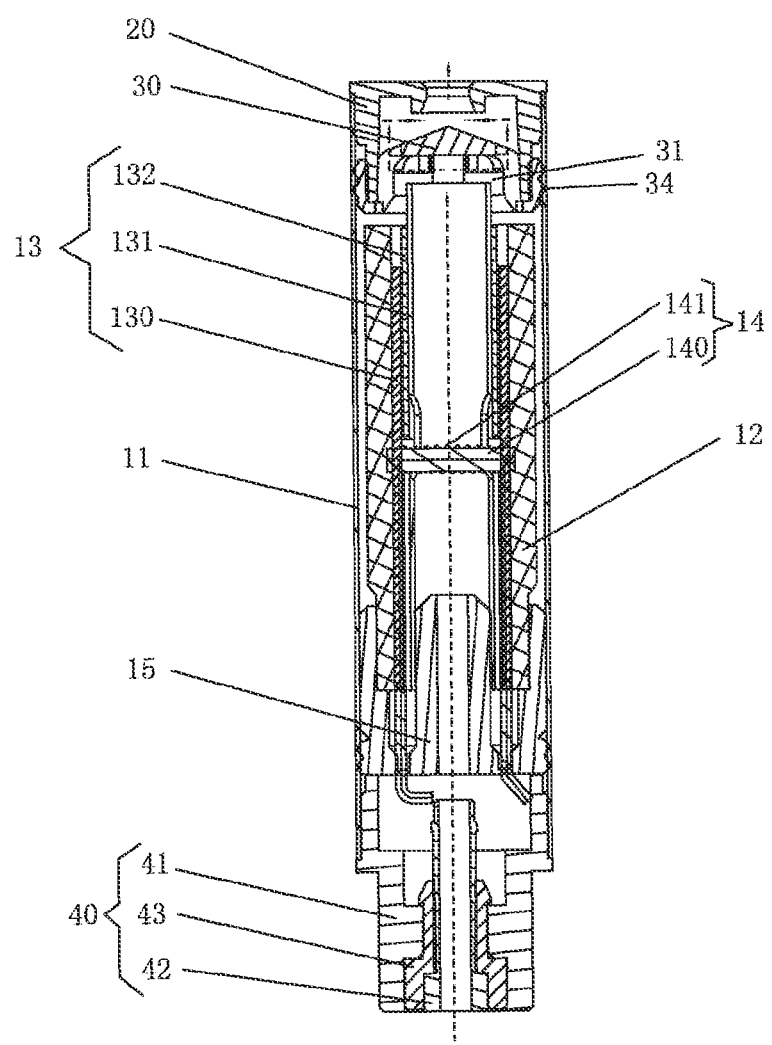
FIG. 3 is a cross-sectional view of the electronic cigarette nozzle as shown in FIG. 1.
Figure 4:
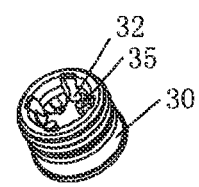
FIG. 4 is an isometric view of a hermetic ring of the electronic cigarette nozzle in accordance with the embodiment of the present invention.
Figure 5:
FIG. 5 is a schematic structural view of the hermetic ring as shown in FIG. 3.
Figure 6:
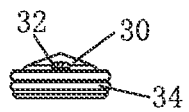
FIG. 6 is a side view of the hermetic ring as shown in FIG. 4.
Figure 7:
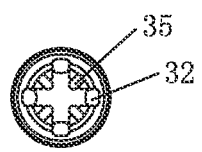
FIG. 7 is a schematic view of the hermetic ring as shown in FIG. 4 in another perspective.

Please refer to FIGS. 1-7, the embodiment of the present invention provides an electronic cigarette and its nozzle, the electronic cigarette nozzle comprises an atomizer 10, a nozzle cover 20 configured at an end of the atomizer 10, a hermetic ring 30 hermetically configured between the atomizer 10 and the nozzle cover 20, and a first connector 40 configured at another end of the atomizer 10.

The atomizer 10 comprises a hollow tubular-shaped atomizing sleeve 11, an oil-storage cotton 12, a protection tube 13, an atomizing unit 14 and an atomizing seat 15.

The oil-storage cotton 12 is fixed within the atomizing sleeve 11, and is also hollow tubular-shaped and configured to be coaxial with the atomizing sleeve 11.

The protection tube 13 is affixed onto an inner wall of the oil-storage cotton 12, and comprises a heat-resistant layer 130, a first fiberglass tube 131 and a second fiberglass tube 132. Wherein, the heat-resistant layer 130 is affixed onto the inner wall of the oil-storage cotton 12 and coaxial with the oil-storage cotton 12; the heat-resistant layer 130 is made of a material, such heat-resistant cotton cloth, plastic etc., the first fiberglass tube 131 is coaxially configured at an inner side of the heat-resistant layer 130; the second fiberglass tube 132 is affixed to an outer wall of the first fiberglass tube 131 and the inner wall of the heat-resistant layer 130 and located at an end facing to the nozzle cover 20. Therefore, the heat-resistant layer 130, the first fiberglass tube 131 and the second fiberglass tube 132 commonly construct a protective structure having heat-resistance, and anti-crushing functions. Moreover, the second fiberglass tube 132 is totally clamped and fixed between the heat-resistant layer 130 and the first fiberglass tube 131 after being installed, and its one end abuts against the atomizing unit 14, concretely, the first fiberglass tube 131 defines a pair of perforations (not labeled) in a radial direction thereof for the atomizing unit 14 to pass through, in order to facilitate installation, the perforations tend to be relatively big, the end of the second fiberglass tube 132 abutting against the atomizing unit 14 makes the atomizing unit 14 tightly fixed in the perforations, for preventing the atomizing unit 14 from movement.

The atomizing unit 14 is configured within the protection tube 13, and comprises an oil guiding member 140 and a heating wire 141. Wherein, the oil guiding member 140 has its opposite ends to pass through the first fiberglass tube 131 of the protection tube 13 and abut against the oil-storage cotton 12, to absorb smoke oil from the oil-storage cotton 12, and the heating wire 141 is wound around the oil guiding member 140 for heating and atomization.

The atomizing seat 15 is hermetically fixed to an end of a tube constituted by the oil-storage cotton 12 and the protection tube 13 and remote from the nozzle cover, and is made of silicone material.

The nozzle cover 20 is substantially barrel-shaped, and defines a suction hole (not labeled) for user to suck the electronic cigarette.

The hermetic ring 30 defines an concave chamber 31 oriented to the atomizer 10, a thickness of the top wall of the concave chamber 21 is gradually increased from a circumference to a center so that an upper surface of the top wall is a bevel, and plural through holes 32 are circumferentially defined through the top wall. Therefore, the smoke oil is heated up and atomized into vapor in the atomizer 10, the vapor passes through a space constituted by the nozzle cover 20 and the top wall of the concave chamber 31 of the hermetical ring 30 and is partially liquefied to be smoke oil in case of cold, the liquefied smoke oil is gathered on the upper surface of the top wall, and since the upper surface of the top wall is a bevel, the smoke oil flows down along the upper surface to the circumference of the bottom top wall by gravity, and flows out of the space constituted by the nozzle cover 20 and the top wall of the concave chamber 31 of the hermetical ring 30 via the through holes 32, to thereby eliminate the smoke oil residue, and the users would not inhale the smoke oil, and can have an improved taste experience.

The hermetic ring 30 defines a circumferential slot 33 oriented to the nozzle cover 20 and coaxial with the concave chamber 31, and the slot 33 is used for accommodating a side wall of the nozzle cover 20, to thereby hermetically fix the nozzle cover 20. Additionally, during assembly, the hermetic ring 30 and the nozzle cover 20 are assembled together firstly, and then totally installed into the atomizing sleeve 11, to prevent the hermitic ring 30 from slanting if installed afterwards which can cause oil leakage or no ventilation. The slot 33 is circumferentially configured with stripes 34 on an outer surface of its side wall, and the stripes 34 are interferentially and hermetically engaged with the atomizing sleeve 11. Furthermore, the nozzle cover 20 has a stepped outer side, and a step 21 near the suction hole is interferentially engaged with the inner wall of the atomizing sleeve 11, therefore, the atomizing sleeve 11 is dual-sealed by means of the stripes 24 and the step 21, to efficiently prevent the smoke oil in the oil-storage cotton 12 from leakage via the nozzle cover 20.

The concave chamber 31 on a lower surface of its top wall is configured with plural ribs 35 having a pre-determined height, the ribs 35 and the through holes 32 are alternately arranged, and the ribs 35 have a pre-determined radial length, and the radial length is less than a corresponding surface radius of the top wall. The ribs 35 having the pre-determined height and length, efficiently prevent the first fiberglass tube 31 which has one end inserted into the concave chamber 31 of the hermetical ring 30 from reaching the top wall of the concave chamber 31, and further prevent the first fiberglass tube 131 from being sealed, to ensure good ventilation. Additionally, the suction hole, a space defined by the nozzle cover 20 and the top wall of the hermetical ring 30, the through holes 32 of the hermetical ring 30, a space defined by adjacent ribs 35 and having a pre-determined height, and the protection tube 13 orderly constitute a smog passage, compared to the conventional linear smog passage through which the smoke particles and broken fiberglass particles generated in course of a use of the atomizer 10 would straightly go into the user's mouth, the smog passage of the present invention is a curve-shaped passage, the smog goes into the user's mouth after a divergence toward the surrounding, this can decrease the airflow intensity, and efficiently obstruct the above-said particles, and the particles would fall back by gravity and are absorbed by the oil-storage cotton 12.

The first connector 40 is configured at an end of the atomizer 10 remote from the nozzle cover 20, used for mating with a power rod of the electronic cigarette. The first connector 40 comprises a first connecting seat 41, a first pole 42 and a first insulating sleeve 43. Wherein the first connecting seat 41 serves as a first electrode, the first pole is coaxially configured within the first connecting seat 41, and serves as a second electrode; the first insulating sleeve 43 is configured between the first connecting seat 41 and the first pole 42 to insulate them. Lead wires connected with opposite ends of the heating wire 141 pass through the first fiberglass tube 131, the atomizing seat 15 and then are respectively electrically connected with the first connecting seat 41 and the first pole 42.

The electronic cigarette of the present invention comprises the electronic cigarette nozzle and a power rod (not shown) connected with the electronic cigarette nozzle. The power rod is configured with a battery therein, and the power rod is further configured with a second connector at its end to mate with the electronic cigarette nozzle. The second connector comprises a second connecting seat, a second pole and a second insulating sleeve. Wherein the second connecting seat serves as a first electrode, the second pole is coaxially configured within the first connecting seat, and serves as a second electrode, the second insulating sleeve is configured between the second connecting seat and the second pole to insulate them, after the two connectors are installed, the two first electrodes are correspondingly connected with each other, the two second electrodes are correspondingly connected with each other, and the second connecting seat and the second pole are respectively connected with the positive and negative of the battery within the power rod.

The process for generating airflow of the electronic cigarette in the present invention is that: when the user sucks the electronic cigarette, atmosphere flows into a corresponding hole of the first pole via the power rod or from the outside, and passes through the atomizing seat 15 into the first fiberglass tube 131, and then is mixed with the smog formed by atomization of the atomizing unit 14, and flows into the concave chamber 31 of the hermetical ring 30, after that it is dissipated out via the through holes 32 of the hermetical ring 30, finally enters the user's mouth through the suction hole of the nozzle cover 20.

Though the embodiments of the present invention have been illustrated and described, for the persons of ordinary skill in this field, various changes, modifications, replacement and variations within the principle and spirit of the present invention can be made to the embodiments, the protecting scope of the present invention is defined by the appended claims and their equivalents.

What is claimed is:

1. An electronic cigarette nozzle, comprising an atomizer, and a nozzle cover configured at an end of the atomizer, wherein the electronic cigarette nozzle further comprises a hermetic ring without a center hole hermetically configured between the atomizer and the nozzle cover, the hermetic ring without a center hole defines an concave chamber oriented to the atomizer, a thickness of the top wall of the concave chamber is gradually increased from a circumference to a center so that an upper surface of the top wall is a bevel, and plural through holes are circumferentially defined in the top wall; the concave chamber on a lower surface of its top wall is configured with plural ribs having a pre-determined height and alternately arranged with the through holes, and the ribs have a pre-determined radial length.

2. The electronic cigarette nozzle as described in claim 1, wherein the hermetic ring without a center hole defines a circumferential slot oriented to the nozzle cover and coaxial with the concave chamber, for accommodating a side wall of the nozzle cover.

3. The electronic cigarette nozzle as described in claim 2, wherein the slot is circumferentially configured with stripes on an outer surface of its side wall, to interferentially and hermetically engage with the atomizer.

4. The electronic cigarette nozzle as described in claim 1, wherein the atomizer comprises a hollow tubular-shaped atomizing sleeve, an oil-storage cotton which is coaxially fixed within the atomizing sleeve and hollow tubular-shaped, a protection tube affixed to an inner wall of the oil-storage cotton, an atomizing unit configured within the protection tube and an atomizing seat hermetically fixed to an end of a tube constituted by the oil-storage cotton and the protection tube and remote from the nozzle cover.

5. The electronic cigarette nozzle as described in claim 4, wherein the protection tube comprises a heat-resistant layer affixed onto the inner wall of the oil-storage cotton and coaxial with the oil-storage cotton, a first fiberglass tube coaxially configured at an inner side of the heat-resistant layer, and a second fiberglass tube affixed to an outer wall of the first fiberglass tube and an inner wall of the heat-resistant layer and located at an end facing to the nozzle cover, the first fiberglass tube has its one end inserted into the concave chamber of the hermetic ring without a center hole, and the second fiberglass tube has its one end to abut against the atomizing unit.

6. The electronic cigarette nozzle as described in claim 5, wherein the nozzle cover defines a suction hole, and the suction hole, a space defined by the nozzle cover and the top wall of the hermetical ring without a center hole, the through holes of the hermetical ring without a center hole, a space defined by adjacent ribs and having a pre-determined height, and the protection tube orderly constitute a smog passage.

7. The electronic cigarette nozzle as described in claim 4, wherein the atomizing unit comprises an oil guiding member having its opposite ends to pass through the protection tube and abut against the oil-storage cotton, and a heating wire wound around the oil guiding member.

8. The electronic cigarette nozzle as described in claim 5, wherein the atomizer is configured with a first connector at its end remote from the nozzle cover for mating with a power rod of the electronic cigarette, the first connector comprises a first connecting seat serving as a first electrode, a first pole coaxially configured within the first connecting seat and serving as a second electrode, and a first insulating sleeve configured between the first connecting seat and the first pole to insulate them.

9. The electronic cigarette nozzle as described in claim 8, wherein lead wires connected with opposite ends of the heating wire pass through the first fiberglass tube, the atomizing seat and are respectively electrically connected with the first connecting seat and the first pole.

10. An electronic cigarette, wherein the electronic cigarette comprises an electronic cigarette nozzle and a power rod connected with the electronic cigarette nozzle, wherein the electronic cigarette nozzle comprises an atomizer, a nozzle cover configured at an end of the atomizer, a hermetic ring without a center hole hermetically configured between the atomizer and the nozzle cover, the hermetic ring without a center hole defines an concave chamber oriented to the atomizer, a thickness of the top wall of the concave chamber is gradually increased from a circumference to a center so that an upper surface of the top wall is a bevel, and plural through holes are circumferentially defined in the top wall; the concave chamber on a lower surface of its top wall is configured with plural ribs having a pre-determined height and alternately arranged with the through holes, and the ribs have a pre-determined radial length.

11. The electronic cigarette as described in claim 10, wherein the power rod is configured with a battery therein, and the power rod is further configured with a second connector at its end to mate with the electronic cigarette nozzle.

12. The electronic cigarette as described in claim 11, wherein the second connector comprises a second connecting seat serving as a first electrode, a second pole coaxially configured within the second connecting seat and serving as a second electrode, a second insulating sleeve configured between the second connecting seat and the second pole to insulate them.

* * * * *